(12) United States Patent
Nguyen et al.

(10) Patent No.: US 6,221,404 B1
(45) Date of Patent: Apr. 24, 2001

(54) METHOD FOR IMPROVING THE EFFICACY OF A PROBIOTIC, PREPARATION OF FOOD ADDITIVES AND ANIMAL FEED CONTAINING SAME

(75) Inventors: Tan Hung Nguyen, Saint-Ave; Alain Guyonvarch, Vannes; Isabelle Brongniart, Trefflean, all of (FR)

(73) Assignee: Hoechst Roussel Vet S.A., Romainville (FR)

( * ) Notice: Subject to any disclaimer, the term of this patent is extended or adjusted under 35 U.S.C. 154(b) by 0 days.

(21) Appl. No.: 09/446,512

(22) PCT Filed: Jun. 25, 1998

(86) PCT No.: PCT/FR98/01348

§ 371 Date: Apr. 7, 2000

§ 102(e) Date: Apr. 7, 2000

(87) PCT Pub. No.: WO99/00022

PCT Pub. Date: Jan. 7, 1999

(30) Foreign Application Priority Data

Jun. 27, 1997 (FR) .................................................. 97 08113

(51) Int. Cl.$^7$ ................................ A23K 1/18; A23K 1/17
(52) U.S. Cl. .................................. 426/2; 426/53; 426/807
(58) Field of Search .................................. 426/2, 53, 807

(56) References Cited

FOREIGN PATENT DOCUMENTS 0 296 051  12/1988  (EP) .
2 450 110   9/1980  (FR) .

*Primary Examiner*—Chhaya D. Sayala
(74) *Attorney, Agent, or Firm*—Burns, Doane, Swecker & Mathis, L.L.P.

(57) ABSTRACT

The invention concerns a method for improving the zootechnic efficacy of the probiotic consisting of *Bacillus sereus* CIP 5832 whereby the probiotic and lysozyme are administered to the animals, preferably simultaneously.

6 Claims, No Drawings

METHOD FOR IMPROVING THE EFFICACY OF A PROBIOTIC, PREPARATION OF FOOD ADDITIVES AND ANIMAL FEED CONTAINING SAME

Method for improving the efficacy of a probiotic, preparation of nutritional additives, and animal feed containing it.

The present invention relates to a method for improving the zootechnic efficacy of the probiotic constituted by *Bacillus cereus* CIP 5832, a preparation of nonmedicinal nutritional additives, and the animal feed containing it.

The probiotics constitute a class of nonmedicinal nutritional additives which are used increasingly in animal production and animal nutrition.

Probiotics are live microorganisms which, once they are ingested, are capable of improving the zootechnic performances of the animals, both in mammals and in birds. The zootechnic performances which are most sought after by livestock breeders are the growth of the animals and their feed conversion index (amount of feed required for producing one unit of weight gain).

A number of species and strains of bacteria, yeasts or fungi have been proposed as probiotics.

The most frequently used method of administering a probiotic is incorporation of the additive into the feed or the drinking water of the animals.

Whether in the feed or in the drinking water, in order for the probiotic to be efficacious it is necessary for the physiological integrity of the microorganism which constitutes it to be preserved and for the microorganism to remain alive.

Thus, patent FR-2 616 662 teaches that *Bacillus cereus* CIP 5832 increases the growth and reduces the feed conversion index of several animal species, both birds and mammals. To achieve these zootechnic effects, the probiotic must be incorporated at 100,000 to 5,000,000 revivable microorganisms per gram of feed.

The patent EP-0 399 819 teaches that the efficacy of the probiotic constituted by *Bacillus cereus* var. toyoi can be preserved by protecting its integrity by incorporating the probiotic into a carbohydrate obtained from a cereal.

R. HAVENAAR et al. (Selection of strains for probiotic use. In Probiotics. The Scientific Basis. Edited by R. FULLER. Chapman & Hall Ed., 1992, pages 209–224) have described the in vitro selection criteria for microorganisms which can be used as probiotics. Amongst those criteria, resistance to antibiotics and to antimicrobial substances is a necessity.

Lysozyme is a natural antimicrobial polypeptide found in a number of organs or body fluids of humans and animals, and even of plants. Thus, lysozyme can be isolated from milk, tear fluid, saliva and nasal mucus of humans. It is found in the milk and the colostrum of cows. It has also been possible to isolate the lysozyme from cauliflower juice. However, the most important source which allows lysozyme to be extracted on an industrial scale is chicken albumen.

Lysozyme is an enzyme (muramidase, E.C. 3.2.1.17) capable of lysing the bond between N-acetylmuramic acid and the N-acetylglucosamine of peptidoglycans which are found in large quantities in the walls of gram-positive bacteria. This is why lysozyme has an antimicrobial action on gram-positive bacteria. Amongst this group of bacteria, *Bacillus cereus* is sensitive to the inhibitory action of lysozyme.

This antimicrobial property of lysozyme allows it to be currently used as a preservative in human nutrition and as a medicament in human pharmacology.

Patent FR-2 450 110 teaches that lysozyme can be used for treating domestic animals, both mammals or birds.

This patent claims:

1. A composition for treating animals which are suffering from an infection caused by microorganisms, characterized in that it comprises, as active principle, lysozyme or a nontoxic salt of the latter.
2. Solid or liquid nutritional products for domestic animals, characterized in that they comprise lysozyme and/or at least one nontoxic salt of the latter.
3. Feed for domestic animals, characterized in that it comprises lysozyme and/or at least one nontoxic salt of the latter.

K. KOUDELA et al. (Zivocisna Vyroba, 1995, 40(7), 313–317) have demonstrated that lysozyme has beneficial effects on the growth and the feed conversion index of chickens which ingest 5, 10, 15 and 20 milligrams of lysozyme per kilogram of feed. Growth and feed conversion index were improved while the plasma corticosterone concentrations of the chickens remained the same.

Even though *Bacillus cereus* CIP 5832 is inhibited in vitro by lysozyme, it has been found unexpectedly that the advantageous zootechnic effects of this probiotic are intensified in vivo in animals, both mammals and birds, by adminstration of lysozyme by the oral route, preferably simultaneously.

The present invention therefore relates to the use of lysozyme for intensifying the zootechnic effects of the probiotic constituted by *Bacillus cereus* CIP 5832.

As far as we known, this synergism between lysozyme and a Bacillus has never been described and, naturally, the mechanism which can explain this synergistic action is unknown.

The use doses of the probiotic constituted by *Bacillus cereus* CIP 5832 are those currently used for this probiotic, viz. 100,000 to 5,000,000 revivable microorganisms per gram of feed. The administration doses of lysozyme or one of its salts are 5 to 200 milligrams per kilogram of feed, preferably 10 to 100 milligrams per kilogram of feed, depending on the desired technical and economical effect.

The nonexhaustive examples which illustrate the invention are not by way of limitation.

EXAMPLE 1

A PCA plate-count agar (Biokar, Beauvais, France) is poured into two Petri dishes and, when solid, surface-inoculated with a culture of Bacillus cereus CIP 5832.

Using a hollow punch, five wells of 10 mm diameter are punched into the agar of each Petri dish.

125 µl of water are introduced into the first well of each Petri dish, and 125 µl of aqueous solutions of lysozyme-hydrochloride (Ovonor, Béthune, France) with a titer of 10, 50, 100 and 1000 mg/liter respectively are introduced into the remaining four wells.

The Petri dishes are incubated for 48 hours in the oven at 37° C.

After incubation, the following results are observed: the characteristic colonies of *Bacillus cereus* CIP 5832 have developed on the agar surface.

Around the wells which contain the lysozyme solutions, a clear zone is observed which demonstrates a certain inhibition of the Bacillus. This zone does not exist around the well which only contains water. The zone diameters are as follows:

| Lysozyme (mg/liter) | Zone diameter (mm) |
|---|---|
| 10 | 12.0 |
| 50 | 14.5 |
| 100 | 16.5 |
| 1000 | 20.3 |

EXAMPLE 2

Some 96 perfectly healthy piglets are divided into three homogeneous groups of 32 animals each. During the 27-day-long experiment, each group receives one of three feeds which have the same basic composition, but differ with regard to their supplementation with additives.

The basic feed was formulated to provide the following nutrients:

| Net energy | 2300 kcal/kg |
|---|---|
| Proteins | 17.00% |
| Available lysine | 1.00% |
| Available methionine | 0.35% |
| Available threonine | 0.61% |
| Fats | 2.17% |
| Cellulose | 3.14% |
| Calcium | 0.77% |
| Phosphorus | 0.59% |

The three groups receive the following supplementation with additives:
GROUP 1: *Bacillus cereus* CIP 5832 (Paciflor C10, N.D., Prodera, Vannes, France). 1,000,000 revivable microorganisms per gram of feed.
GROUP 2: *Bacillus cereus* CIP 5832 1,000.000 microorganisms per gram of feed plus lysozyme-hydrochloride (Ovonor, Béthune, France). 10 mg per kilogram of feed.
GROUP 3: *Bacillus cereus* CIP 5832 1,000,000 revivable microorganisms per gram of feed plus lysozyme-hydrochloride. 50 mg per kilogram of feed.

During the experiment, the piglets were allowed to feed and drink ad libitum.

The zootechnic performance measured was:
initial live weight and final live weight, from which the growth rate expressed by average daily weight gain can be calculated, and
consumption of feed divided by weight gain, which gives the feed conversion index.

The average results obtained during this 27-day experiment are as follows:

|  | GROUP 1 | GROUP 2 | GROUP 3 |
|---|---|---|---|
| Initial live weight (kg) | 14.2 | 14.2 | 14.2 |
| Final live weight (kg) | 29.5 | 29.8 | 30.7 |
| Daily weight gain (g/day) | 566 (100%) | 577 (101.9%) | 611 (107.9%) |
| Feed consumption (g/day) | 978 | 954 | 1005 |
| Feed conversion index | 1.72 (100%) | 1.65 (95.9%) | 1.64 (95.3%) |

These results demonstrate that the combinations of *Bacillus cereus* CIP 5832 and lysozyme result in better zootechnic performance of the piglets compared with that obtained only with *Bacillus cereus* CIP 5832. It must be noted that the piglets of this experiment are perfectly healthy and not animals which are suffering from an infection caused by microorganisms, as is mentioned in the claim of the above-mentioned patent FR-2 450 110.

EXAMPLE 3

240 male one-day-old chicks are divided into four groups of 60 animals each. The birds are kept in wire-mesh cages at a stock density of 20 animals per cage and are allowed to feed and drink ad libitum.

During the 21-day-long experiment, each of the 4 groups of chicks receives one of the 4 experimental feeds which have the same basic formula but contain different supplementations.

The basic formula provides the following nutrients:

| Metabolizable energy | 11.8 MJ/kg |
|---|---|
| Crude protein | 22.0% |
| Fats | 3.7% |
| Cellulose | 2.8 |
| Minerals | 6.1 |
| Nitrogen-free extracts | 53.4% |

The supplementations are as follows:
GROUP 1 : no additive (negative control)
GROUP 2 : *Bacillus cereus* CIP 5832 at a concentration of 500,000 revivable microorganisms per gram of feed.
GROUP 3 : 10 milligrams of lysozyme-hydrochloride per kilogram of feed.
GROUP 4: *Bacillus cereus* CIP 5832 at a concentration of 500,000 revivable microorganisms per gram of feed plus 10 milligrams of lysozyme-hydrochloride per kilogram of feed.

The *Bacillus cereus* CIP 5832 and the lysozyme-hydrochloride were supplied by the same suppliers as in the previous example.

After an experimental time of 21 days, the growth of the animals expressed by the final weight and their feed conversion index are as follows:

|  | GROUP 1 | GROUP 2 | GROUP 3 | GROUP 4 |
|---|---|---|---|---|
| Live weight (g) | 568 (100%) | 608 (107%) | 546 (96.1%) | 622 (109.5%) |
| Feed conversion index | 1.575 (100%) | 1.506 (95.6%) | 1.560 (99.0%) | 1.502 (95.3%) |

These results demonstrate that:
*Bacillus cereus* CIP 5832 alone improves the zootechnic performance of the chicks (Group 2 compared with Group 1):
lysozyme alone did not improve the growth of the chicks, and its effect on the feed conversion index is quite low (Group 3 compared with Group 1);
the simultaneous administration of lysozyme improves the zootechnic performance of the probiotic (Group 4 compared with Group 2).

What is claimed is:

1. A method for improving the zootechnic efficacy of the probiotic constituted by *Bacillus cereus* CIP 5832, comprising administering the probiotic and lysozyme or one of its salts to the animals by the oral route.

2. A method according to claim 1, comprising administering to the animals 100,000 to 5,000,000 revivable *Bacillus cereus* CIP 5832 microorganisms per gram of feed, plus 5 to 200 milligrams of lysozyme or one of its salts per kilogram of feed.

3. A method according to claim 1, comprising administering the probiotic and lysozyme or one of its salts simultaneously.

4. A method according to claim 2, comprising administering the probiotic and lysozyme or one of its salts simultaneously.

5. A preparation of nonmedicinal nutritional additives, comprising *Bacillus cereus* CIP 5832 and lysozyme or one of its salts.

6. An animal feed containing the additive, *Bacillus cereus* CIP 5832 together with lysozyme or one of its salts.

* * * * *